United States Patent
Bonelli et al.

(10) Patent No.: US 8,029,483 B2
(45) Date of Patent: Oct. 4, 2011

(54) DISPOSABLE ABSORBENT ARTICLES HAVING IMPROVED ADHESIVE FOR GARMENT FASTENING

(75) Inventors: Guido Bonelli, Pescara (IT); Ivano Gagliardi, Pescara (IT); Magali Fabienne Pourcel, Pescara (IT); Fiorello Salone, Pescara (IT)

(73) Assignee: The Procter & Gamble Company, Cincinnati, OH (US)

(*) Notice: Subject to any disclaimer, the term of this patent is extended or adjusted under 35 U.S.C. 154(b) by 901 days.

(21) Appl. No.: 11/811,035

(22) Filed: Jun. 8, 2007

(65) Prior Publication Data

US 2007/0287974 A1    Dec. 13, 2007

(51) Int. Cl.
*A61F 13/15* (2006.01)
*A61F 13/20* (2006.01)

(52) U.S. Cl. ............ 604/385.03; 607/387

(58) Field of Classification Search ........... 604/385.01, 604/385.03, 332, 344, 387
See application file for complete search history.

(56) References Cited

U.S. PATENT DOCUMENTS

| 5,128,187 A | 7/1992 | Polski |
| 6,004,308 A | 12/1999 | Haddock |
| 6,180,229 B1 | 1/2001 | Becker et al. |
| 6,685,683 B1 * | 2/2004 | Clok et al. ............. 604/344 |
| 7,842,022 B2 | 11/2010 | Veglio et al. |
| 2004/0266965 A1 * | 12/2004 | Holguin et al. .......... 526/320 |
| 2005/0256481 A1 | 11/2005 | Rosati et al. |

FOREIGN PATENT DOCUMENTS

| EP | 0 140 135 A1 | 5/1985 |
| SE | 374489 A | 3/1975 |
| WO | WO 00/61054 A1 | 10/2000 |
| WO | WO 01/14487 | 3/2001 |

OTHER PUBLICATIONS

PCT International Search Report dated Mar. 26, 2008.

* cited by examiner

*Primary Examiner* — Melanie Hand
(74) *Attorney, Agent, or Firm* — Amanda T. Barry

(57) ABSTRACT

An absorbent article for personal hygiene, especially a sanitary napkin, panty liner and the like, having an adhesive for securing the article to a garment of a wearer. The present invention provides adhesives with an adhesion performance less dependent from panty material types and washing habits, such as treatment with softeners and the like, thus ensuring reliable fastening on non-treated panties as well as on softener-treated panties.

6 Claims, No Drawings

DISPOSABLE ABSORBENT ARTICLES HAVING IMPROVED ADHESIVE FOR GARMENT FASTENING

FIELD OF THE INVENTION

The present invention relates to an absorbent article for personal hygiene, especially a sanitary napkin, panty liner and the like, comprising an adhesive for securing the article to the garments of a wearer. The present invention provides adhesives with an adhesion performance less dependent from panty material types and washing habits, such as treatment with softeners and the like, and thus insuring reliable fastening on non-treated panties as well as on softener-treated panties. Further, the adhesives of the present invention have an especially low variation between the peel strength when peeling off the absorbent article and when wearing the absorbent article.

BACKGROUND OF THE INVENTION

The use of adhesives for securing disposable absorbent articles for personal hygiene is well known in the art. In particular, the use of hot melt and emulsion-based adhesives is general technical standard. The application of emulsion-based adhesives onto the backsheets of absorbent articles for garment fastening is for instance known from SE-A-374,489. The use of hot melt adhesives for this purpose is for instance described in EP-A-140,135 or in WO 00/61054.

It is very common to apply fabric softeners after washing the undergarments for improving fabric softness. Fabric softeners act on the garment fabric by modifying the surface properties of the fabric fibres. One of the effects of softeners is to make the fibre surfaces more hydrophobic, e.g. by depositing a thin layer of fat-like molecules.

These surface treatments have been found to be detrimental for the fastening performance of conventional adhesives used for fastening absorbent articles to undergarments, such as panties. These adhesives are called panty-fastening adhesives or PFAs hereinafter. Laboratory experiments and consumer feedback have proven that softener treatments significantly reduce the peel strength of conventional PFAs.

Therefore it would be beneficial to provide PFAs having similar fastening performance on both untreated and softener-treated panties.

Further it would be beneficial if such adhesives had similar peel strength during the wearing time from application onto panties to removal, so as to insure an improved adhesion level throughout its use.

SUMMARY OF THE INVENTION

In order to solve the problems discussed above, the present invention provides a disposable absorbent article for personal hygiene, said article having a wearer-facing surface and a garment-facing surface, said garment-facing surface comprising an adhesive for attachment of said article to the garment of a wearer, characterized in that the adhesive on said garment-facing surface has a ΔP of not more than 35%, and a ΔS of not more than 25%.

DETAILED DESCRIPTION OF THE INVENTION

The term 'absorbent article' is used herein in a very broad sense including any article being able to receive and/or absorb and/or contain and/or retain fluids and/or exudates, especially bodily fluids/bodily exudates. The absorbent article, which is referred to in the present invention typically comprises a fluid pervious topsheet as the wearer-facing surface, a fluid impervious backsheet as the garment-facing surface that is typically water vapour and/or gas pervious and an absorbent core comprised there between. Furthermore, absorbent articles in the context of the present invention are provided with a means for their attachment to the user's garment, in particular with an adhesive. Typical absorbent articles in the context of the present invention are disposable absorbent articles. Typical disposable absorbent articles according to the present invention are absorbent articles for personal hygiene, such as baby care articles like baby diapers; incontinence pads and perspiration pads like underarm sweat pads or hat bands. Typical disposable absorbent articles are absorbent articles for feminine hygiene like sanitary napkins and panty liners and incontinence pads.

By 'body fluid' it is meant herein any fluid produced by the human body including for instance perspiration, urine, blood, menstrual fluids, vaginal secretions and the like.

The term 'disposable' is used herein to describe articles, which are not intended to be laundered or otherwise restored or reused as an article (i.e. they are intended to be discarded after a single use and conventionally to be recycled, composted or otherwise disposed of in an environmentally compatible manner).

The term 'use', as used herein, refers to the period of time that starts when the absorbent article is actually put in contact with the anatomy or in clothing of the user and that lasts until removal of the absorbent article for disposal.

As used herein, 'hydrophilic' refers to a material having a contact angle of water in air of less than 90 degrees, whereas the term 'hydrophobic' herein refers to a material having a contact angle of water in air of 90 degrees or greater. Hydrophobic materials are also referred to as water-repellent.

As said infra, an absorbent article in the context of the present invention comprises an adhesive means for the attachment of this article to the user's garments. This adhesive is also referred to as 'panty fastening adhesive' or 'PFA'. The PFA is provided on the garment facing surface of the absorbent article of the present invention, typically the backsheet, for attaching said article to the garment of a wearer. Similarly, if the product is a winged product, the wings can also be provided with PFA on the garment-facing surface in order to secure the wings to the wearer's garment. The PFA for use herein is in most cases a pressure-sensitive adhesive, typically a hot melt pressure-sensitive adhesive.

'Softeners' or 'fabric softeners' herein are compositions. Fabric softeners are widely known in the art. Examples are quaternary ammonium compounds suitable for softening fabric in a rinse step, as well as esters obtainable from the reaction of fatty acids and amino alcohols. Example of commercial softener is "LENOR" or "DOWNY" commercialized by The Procter and Gamble Company.

The Panty-Fastening Adhesive (PFA)

The backsheet typically forms the garment-facing surface of the absorbent article on which the panty fastening adhesive is placed. Panty-fastening adhesives can comprise any adhesive or glue used in the art for such purposes. These adhesives typically are pressure sensitive and remain tacky well below their application temperature. Conventional adhesives used therefore are for example Savare LA203 and Savare LA303 made by Savare I.C. of Milan in Italy, Coramelt 867 by Koemmerling in Pirmasens in Germany, Fuller D3964ZP, Fuller H-2238ZP and Fuller 1461X manufactured by the H.B. Fuller Co. in Lueneburg, in Germany, NS34-2823 as manufactured by National Starch and Chemical of Bridgewater, N.J. However, these adhesives have wider delta S and P as reported in table 1 below. The adhesive performance fluctuates too much in respect of washing habits (delta S) and compression during use (delta P) delivering either too low adhesion (in the extreme case of hydrophobic panty and poor compression) or too strong adhesion (in the worst combination of hydrophilic surface and strong compression). Based on these observations the present inventors have found that adhesives being able to overcome the disadvantages have to fulfill two desirable parameters. The adhesives of the present invention should have a $\Delta P$ of not more than 35% and a $\Delta S$ of not more than 25%.

An exemplary PFA fulfilling the above desired qualities of the present invention is MF 112 D, available from Savare I.C. of Milan in Italy. MF 112 D is a pressure sensitive adhesive composition which consists of a mixture of ingredients comprising approximately: (a) 30% by weight of a blend of SIS (styrene-butadiene-styrene) polymers (b) 50% by weight of a blend of tackifying resins and (c) 20% by weight of plasticizers and other components. Viscoelastic characterization by dynamical mechanical analysis shows approximately: (a) a tan $\delta$ peak at 1 Hz at 0° C. (b) a tan $\delta$ at 1 Hz at 0° C. of 3.0 (c) an elastic modulus G' at 25° C. at 1 HZ of 40000 Pa, (d) an elastic modulus G' at 40° C. at 1 HZ of 30000 Pa, (e) a creep deformation at 40° C., 200 Pa, after 660 sec of 1.7%.

The Absorbent Article

The absorbent article of the present invention typically comprises a topsheet as the body-facing surface, a backsheet as the garment-facing surface and an absorbent core disposed therebetween.

The Topsheet

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and non woven materials; polymeric materials such as apertured formed thermoplastic films, apertured plastic films, and hydroformed thermoplastic films; and thermoplastic scrims. Suitable woven and nonwoven materials can be comprised of natural fibres (e.g., wood or cotton fibres), synthetic fibres (e.g., polymeric fibres such as polyester, polypropylene, or polyethylene fibres) or from a combination of natural and synthetic fibres or bi-/multi-component fibres.

Typical topsheets for uses in the present invention may be selected from high loft nonwoven topsheets and apertured formed film topsheets. Apertured formed films are very common for topsheets because they are pervious to body exudates and yet non absorbent and have a reduced tendency to allow fluids to pass back through and rewet the wearer's skin. Thus, the surface of the formed film that is in contact with the body remains dry; thereby reducing body soiling and creating a more comfortable feel for the wearer. Suitable formed films are described in U.S. Pat. No. 3,929,135; U.S. Pat. No. 4,324,246; U.S. Pat. No. 4,342,314; U.S. Pat. No. 4,463,045; and U.S. Pat. No. 5,006,394. Particular micro apertured formed film topsheets are disclosed in U.S. Pat. No. 4,609,518 and U.S. Pat. No. 4,629,643. A exemplary topsheet for the present invention comprises the formed film described in one or more of the above patents and marketed on sanitary napkins by The Procter & Gamble Company of Cincinnati, Ohio as "DRI-WEAVE".

Topsheets having non-homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The body surface of the formed film topsheet can be hydrophilic so as to help liquid to transfer though the topsheet faster than if the body surface was not hydrophilic. In a specific embodiment, surfactant is incorporated into the polymeric materials of the formed film topsheet such as is described in PCT publication WO 93/09741. Alternatively, the body surface of the topsheet can be made hydrophilic by treating it with a surfactant such as is described in U.S. Pat. No. 4,950,254.

Other alternatives include so called hybrid topsheets, which incorporate fibrous and film like structures particularly useful embodiments of such hybrid topsheets are disclosed in PCT publications WO 93/09744; WO 93/11725 or WO 93/11726.

The topsheet typically extends across the whole of the absorbent article and outside the area coextensive with the absorbent article. The topsheet can extend and form part or all of the side flaps, side wrapping elements or wings.

When referring to the topsheet a multi layer structure or a monolayer structure is contemplated. The hybrid topsheet mentioned above is such a multi layer design but other multi layer topsheets such as primary and secondary topsheet designs are also considered.

Absorbent Core

According to the present invention the absorbent cores suitable for use herein may be selected from any of the absorbent cores or core system known in the art. As used herein the term absorbent core refers to any material or multiple material layers whose primary function is to absorb, store and distribute fluid.

According to the present invention, the absorbent core can include the following components: (a) an optional primary fluid distribution layer conventionally together with a secondary optional fluid distribution layer; (b) a fluid storage layer; (c) an optional fibrous ("dusting") layer underlying the storage layer; and (d) other optional components. In most cases at least one of said layers comprises absorbent gelling materials usually referred to as "hydrogel", "superabsorbent", "hydrocolloid" materials in combination with suitable carriers.

Backsheet

The backsheet primarily prevents the exudates absorbed and contained in the absorbent article from wetting articles that contact the absorbent product such as underpants, pants, pyjamas and garments. The backsheet is in one embodiment impervious to liquids (e.g. menses, urine and other vaginal fluid discharges) and may be manufactured from thin plastic films or nonwovens, although other flexible liquid impervious materials (like foam materials) can also be used. As used herein, the term "flexible" refers to materials that are compliant and will readily conform to the general shape and contours of the human body. The backsheet also can have elastic characteristics allowing it to stretch in one or more directions.

The backsheet typically extends across the whole of the absorbent article and can extend into and form part of or all of the sideflaps, side wrapping elements or wings, if this article includes such features.

The backsheet of the absorbent article may be breathable such that it is air permeable moisture vapour permeable and thus comprises at least one gas permeable layer. Suitable gas permeable layers include nonwovens, such as like polypropylene spunbonded nonwovens, or apertured films, such as two-dimensional, planar micro and macro-porous films, macroscopically expanded films, formed apertured films and monolithic films. According to the present invention the apertures in said layer may be of any configuration, but are conventionally spherical or oblong and may also be of varying dimensions. The apertures conventionally are evenly distributed across the entire surface of the layer, however layers having only certain regions of the surface having apertures are also envisioned.

Suitable two-dimensional planar layers of the backsheet may be made of any material known in the art, but are typically manufactured from commonly available polymeric materials. Suitable materials are for example Gortex™ or Sympatex™ type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term two-dimensional planar layer refers to layers having a depth of less than 1 mm, conventionally less than 0.5 mm, wherein the apertures have an average uniform diameter along their length and which do not protrude out of the plane of the layer. The apertured materials for use as a backsheet in the present invention may be produced using any of the methods known in the art including those described in EP 293,482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances may have an orifice located at its terminating end. Oftentimes the protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Oftentimes the apertured formed films are uni directional such that they have at least substantially, if not complete one directional fluid transport towards the core.

Suitable macroscopically expanded films for use herein include films as described in, for example, in U.S. Pat. No. 4,637,819 and U.S. Pat. No. 4,591,523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours international S.A, Switzerland such as Pebax™, available from Elf Atochem (France) and Estane™ available from B.F. Goodrich (Belgium).

Suitable backsheets for the present invention may comprise at least two layers including at least one layer selected from the above, such as microporous and apertured formed films and an additional layer which may also be selected from the above listed backsheets or may be a fibrous woven or nonwoven. In one embodiment, the breathable backsheet component comprises a nonwoven and an apertured formed film or a microporous film and a hydrophobic woven or nonwoven material.

The adhesive-coated surfaces are typically provided with protective covers, which are removed prior to use. Prior to use of the absorbent article the areas being coated with PFA are typically protected from contamination and from adhering to another surface, where this is not desired, by a protective cover means such as a silicone coated release paper, a plastic film or any other easily removable cover. The protective cover means can be provided as a single piece or in a multitude of pieces, e.g. to cover the individual adhesive areas. It also can perform other functions such as provide individualised packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

The PFA may be applied to the garment-facing surface of the absorbent article, typically the backsheet or the wings using any one of methods well known in the art for this purpose such as slot coating, spraying and roll printing. With the development of adhesive printing as described for example in EP 745,432, EP 745,433, and EP 745,368 it has now also become possible to provide such panty-fastening adhesive in any desired shape and hence these methods are suitable for use in the present invention. One method of applying the PFA to the garment-facing surface of the absorbent article is the direct coating on the backsheet; another method is printing the PFA onto a release paper, which is then pressed onto the garment-facing surface of the absorbent article. Thereby the PFA is transferred from the release paper to the garment-facing surface of the absorbent article. Such a procedure is described in EP 788,338. Any application pattern known the respective art is suitable for applying the PFA according to the present invention to the garment-facing surface of the absorbent article herein. Illustrative examples are presented in the attached figures. Typically, the panty fastening adhesive is applied in intermittent patterns such as for example micro-sized intermittent dots, intermittent strips, lines or grids or other designed shapes such as circles. However, also completely random PFA patterns are within the scope of the present invention. It may be desirable that the PFA has a surface coverage on the garment-facing surface of the article of at least 30%, typically 40%, oftentimes 50%, in some instances 60% and in certain cases 70-100%, although any percentage of coverage is contemplated.

EXAMPLES

The adhesive layer applied in a typically continuous stripe can have any width or pattern, with a constant or variable basis weight. Typically, the application is in a continuous stripe having constant width and constant basis weight. One application method is hot melt bar coating, also known as slot coating. The adhesive layer can be applied typically with a basis weight from 5 $g/m^2$ to 35 $g/m^2$, in some embodiments from 15 $g/m^2$ and 25 $g/m^2$, in certain applications from 18 $g/m^2$ and 22 $g/m^2$.

The samples analysed and reported in Table 1 were coated directly on a polypropylene spunbond nonwoven using the slot coating technology. The coating was a continuous stripe having a width of 50 mm. Both adhesives were coated at 20 $g/m^2$ balancing the glue penetration fine tuning the melting temperature, the web tension etc. (as people skilled in the art well know), so as to obtain a fresh peel (QRP) strength of 240 g. After two months aging, the samples were analyzed and the data are shown in Table 1 in the column ("A") below:

TABLE 1

|  | QRP (g) cotton A | ACP (g) cotton X | ACP (g) treated cotton Y | ΔS (%) | ΔP (%) |
|---|---|---|---|---|---|
| Reference: Fuller 1461X | 133 | 189 | 89 | 53 | 43 |
| Novel formula: Savare' MF112D | 188 | 246 | 195 | 21 | 31 |

Reference: Fuller 1461X manufactured by the H.B. Fuller Co. in Luneburg, Germany.
Novel formula: Savare' MF112D manufactured by Savare I.C. of Milan, Italy Test Methods QRP (QuickRigid Peel)

An article of the present invention or part thereof (hereinafter sample) comprising on its garment-facing surface the PFA (the sample and PFA being at room temperature), is placed on a rigid support with the surface with the PFA facing upward, away from the support. Then a plate having an opening, which hereinafter is called "measurement window", is placed on top of the sample's surface, which comprises the PFA. The sample dimensions are to be chosen such that the sample at least fits the measurement window having dimension of 54 mm (width)×126 mm (length). The sample is to be placed relative to the measurement window of the plate such that the measurement window is completely filled by the sample. In a typical execution of this test the sample is placed such that its midpoint (intersect of longitudinal and lateral centre lines) is congruent with the midpoint of the measurement window and that the longitudinal centerlines of the sample and the measurement window are parallel. The sample is fixed to the support by grips in a tight and wrinkle-free manner. Then a piece of cotton (100%), known as Weave Style no. 429W, available from Loeffler, Sitter Technic GmbH, Nettersheim, Germany, is placed on top of the surface with the PFA, which is exposed through the measurement window, such that one end of the cotton piece extends about 25 mm from the end of the measurement window with the PFA. The measurement window must be completely covered by the cotton piece. Then, a weight is placed on the thus formed sample-cotton combination for 30 seconds, such that the whole combination is covered and a weight of 26-27 g/cm$^2$ is applied, to ensure that the combination is pressed in a gentle and even manner. Then, Zwick tensile tester (available from Zwick GmbH) is used to measure the peel force required to remove the cotton piece from the sample. Hereto, the support carrying the sample covered by the cotton piece is placed in the lower clamp of the tensile tester and the tail end of the cotton piece (the one opposite to the free 25 mm specified above) is placed in the upper clamp of the tensile tester. The Zwick tensile tester is set on a speed of 102 cm/min. Typically, the clamps are 250 mm spaced apart. It is obvious that any suitable constant rate of elongation tensile tester can be used. Then, within 1 minute after removal of the compression weight, the tensile tester is started. The cotton piece is peeled off from the sample in a direction, which is parallel to the longitudinal dimension of the measurement window. During the peeling procedure the peel force required to peel off the cotton piece along the displacement of the upper clamp, which moved in an angle of 180° with the sample, is measured. The peel force is calculated as the average of the force peaks over a 13 cm path. The first 2.5 cm and last 3.75 cm of the measurement are not taken into account by the calculation of the peel force, to avoid influences of acceleration and deceleration. The above test is for example done on a sample of the shape and size of a regular Always Alldays pantiliner, using a support plate with a measurement window of 54 mm (width)×126 mm (length) and a weight of 2.1 kg with area dimensions 54 mm×140 mm. The method can be easily adjusted by the skilled person for different sample sizes.

ACP (Automated Conditioned Peel)

Same as QRP but with longer compression time (1 hr instead of 30 min, at higher temperature (inside oven) during compression (37±2° C. instead of room temp.) and on two standard materials: (1.) Cotton weaves style 429-W (as already described in the QRP method) and (2.) Cotton weaves treated with softener style PG-429W-T, also available from Loeffler, Sitter Technic GmbH, Nettersheim, Germany.

Criteria

1. ΔS is the % decrease of adhesion strength from ACP on Cotton weave (style#429) that we name for simplicity "X" to adhesion strength of ACP on Cotton weave treated with softener (style# PG-429W-T) that we name "Y". This parameter predicts the adhesion loss of softener treated panties versus untreated panties. Narrower ΔS insure stable performance throughout different panty materials and washing habits. Therefore lower ΔS is preferred herein. ΔS is calculated as follows:

$$(X-Y)/X*100$$

2. ΔP is the % increase from QRP on Cotton weave (style#429) that we name for simplicity "A" to ACP on Cotton weave (style#429) that we name "X". This parameter predicts the adhesion building over time and the strength fluctuation driven by the pressure/time/temp. Narrower ΔP insure stable performance throughout different consumer compression habits, i.e. application compression, wearing compression etc. Therefore lower ΔP is preferred herein. ΔP is calculated as follows:

$$(X-A)/A*100$$

The test methods disclosed herein can also be used for testing absorbent articles, which comprise PFA on their garment-facing surface in a continuous or non-continuous pattern, such as in the form of stripes or dots. In this case the article has to be arranged in respect to the measurement such that the PFA coated area, which is exposed through the measurement window, is maximized.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. In particular it is obvious to the person skilled in the art that the present invention applies to microfibre materials with inherent hydrophobicity as well as to other panty materials, which were subjected to a hydrophobic treatment. It is therefore intended to cover in the appended claims all such changes and modifications that are within the scope of this invention.

What is claimed is:

1. A disposable absorbent article for personal hygiene, the article having a wearer-facing surface and a garment-facing surface, the garment-facing surface comprising an adhesive for attachment of the article to the garment of a wearer,
    wherein the adhesive on the garment-facing surface has a $\Delta P$ of not more than about 35%, and a $\Delta S$ of not more than about 25%.

2. The disposable absorbent article of claim 1, wherein $\Delta P$ is not more than about 25%.

3. The disposable absorbent article of claim 1, wherein $\Delta S$ is not more than about 15%.

4. The absorbent article of claim 1, wherein the garment-facing surface is covered by the adhesive at a surface coverage of at least about 30%.

5. The absorbent article of claim 1, wherein the adhesive is present on the garment-facing surface at a basis weight of from about 1 to about 35 $g/m^2$.

6. The article of any of claim 1, wherein the article is a sanitary napkin, a panty liner, a diaper, an underarm sweat pad, a hatband or an incontinence protection device.

* * * * *